US008545851B2

(12) United States Patent
Oh et al.

(10) Patent No.: US 8,545,851 B2
(45) Date of Patent: Oct. 1, 2013

(54) COMPOSITION FOR IMPROVING INFLAMMATORY DISEASE USING ABH ANTIGENS

(75) Inventors: Jang Hee Oh, Gyeonggi-do (KR); Ji-Yong Jung, Seoul (KR); Dong Hun Lee, Daejeon (KR); Serah Lee, Seoul (KR); Yeon Kyung Kim, Seoul (KR); Jeong-eun Shin, Gyeongsangbuk-do (KR); June Hyunkyung Lee, Seoul (KR); Jin Ho Chung, Seoul (KR)

(73) Assignee: SNU R&DB Foundation, Seoul (KR)

( * ) Notice: Subject to any disclaimer, the term of this patent is extended or adjusted under 35 U.S.C. 154(b) by 0 days.

(21) Appl. No.: 13/143,462

(22) PCT Filed: Jan. 7, 2010

(86) PCT No.: PCT/KR2010/000103
§ 371 (c)(1),
(2), (4) Date: Jul. 6, 2011

(87) PCT Pub. No.: WO2010/079978
PCT Pub. Date: Jul. 15, 2010

(65) Prior Publication Data
US 2011/0274707 A1    Nov. 10, 2011

(30) Foreign Application Priority Data
Jan. 9, 2009    (KR) .................. 10-2009-0002078

(51) Int. Cl.
*A61K 39/00*    (2006.01)

(52) U.S. Cl.
USPC ..... 424/184.1; 514/18.6; 514/18.7; 514/18.8; 514/44 R; 514/23

(58) Field of Classification Search
None
See application file for complete search history.

(56) References Cited

U.S. PATENT DOCUMENTS

| 6,399,758 | B1 * | 6/2002 | Sandrin et al. ............... 536/23.2 |
| 2003/0073822 | A1 * | 4/2003 | Lofling et al. ............. 530/391.1 |
| 2005/0031710 | A1 | 2/2005 | D'Adamo |
| 2006/0002891 | A1 * | 1/2006 | Pouletty ....................... 424/85.2 |
| 2008/0319173 | A1 * | 12/2008 | Lofling et al. ............. 530/391.1 |

FOREIGN PATENT DOCUMENTS

| JP | S59-216821 A | 5/1983 |
| JP | H04-502758 A | 9/1986 |
| JP | H11-506766 A | 6/1999 |
| JP | 2002-512195 A | 4/2002 |
| JP | 2002173438 A | 6/2002 |
| JP | 2003261454 A | 9/2003 |
| JP | 2003267887 A | 9/2003 |
| JP | 2003335656 A | 11/2003 |
| JP | 2006321758 A | 11/2006 |
| JP | 2007008817 A | 1/2007 |
| JP | 2007-507516 A | 3/2007 |
| JP | 2008044887 A | 2/2008 |
| JP | 2008506508 A | 3/2008 |
| WO | 2007041327 A1 | 4/2007 |
| WO | 2007061912 A2 | 5/2007 |
| WO | 2008147111 A2 | 4/2008 |

OTHER PUBLICATIONS

Yu et al., Clin Dev Immunol. 2012;2012:715190. Epub Jan. 23, 2012.*
International Search Report issued Sep. 16, 2010 in connection with PCT International Application No. PCT/KR2010/000103.
Pamela Greenwell, Blood group antigens: molecules seeking a function?*, Glycoconjugate Journal (1997) 14: 159-173.
Kenneth O. Lloyd, The chemistry and immunochemistry of blood group A, B, H, and Lewis antigens: Past, present and future, Glycoconjugate Journal (2000) 17: 531-541.
Yoshiko Mizukawa et al., Fucosyltransferase VII-positive, skin-homing T cells in the blood and skin lesions of atopic dermatitis patients, Experimental Dermatology, (2007) 17: 170-176.
Mizuho Nosaka et al., Aberrant Expression of Histo-blood Group A Type 3 Antigens in Vascular Endothelial Cells in Inflammatory Sites, Journal of Histochemistry & Cytochemistry (2008) vol. 56(3): 223-231.
Vibeke Ravn et al., Tissue distribution of histo-blood group antigens, APMIS (2000) 108: 1-28.
Erik Dabelsteen et al., Pattern of Distribution of Blood Group Antigens on Human Epidermal Cells During Maturation, The Journal of Investigative Dermatology (1984) 82:13-17.
J.N.W.N. Barker et al., Keratinocytes as initiators of inflammation, The Lancet (1991) vol. 337: 211-214.
Brown S J et al., entitled "Altered Immune System Glycosylation Causes Colitis in μ1,2,-Fucosyltransferase Transgenic Mice", Inflamm Bowel Dis, vol. 10, No. 5, Sep. 2004, 546-556.

* cited by examiner

*Primary Examiner* — Michael Szperka
(74) *Attorney, Agent, or Firm* — Amster, Rothstein & Ebenstein LLP

(57) ABSTRACT

The present invention relates to a composition for improving inflammatory disease, and more specifically to a composition for improving inflammatory disease able to improve inflammatory reactions and the barrier function of epithelial tissue such as the skin, to enhance aging resistance and skin elasticity and to prevent or treat aging. The present invention makes it possible to control inflammatory reactions by modulating the expression and modulating the activity of ABH antigens, and thus the composition of the present invention can be employed as a development marker for therapeutic agents designed to soothe or treat or help in the treatment of disease caused by inflammatory reaction in body tissue and notably the skin expressed by ABH antigens, and can be used in the development of external preparations and cosmetics containing external preparations designed for the purposes such as restoration of normal function and moisturization, wrinkle enhancement, whitening and elasticity recovery in skin through modulation of differentiation of keratinocytes and the skin barrier function.

9 Claims, 14 Drawing Sheets

Galβ1→4GlcNac    N-Lac (Precursor of Type O antigen)

Galβ1→4GlcNac
         2
         ↑
Fucα1                H2 (Type O antigen - type 2)

Gal
        2
        ↑
Fucα1                H (Type O antigen - all types)

GalNAcα1→3Gal
            2
            ↑
       Fucα1        A (Type A antigen)

Galα1→3Gal
         2
         ↑
    Fucα1           B (Type B antigen)

Fuc (Fucose)
Gal (Galactose)
GlcNac (N-acetyl glucosamine)
GalNAc (N-acetyl galactosamine)

Fig.1

| Skin disorder (Number of tissue samples) | Stratum granulosum | Upper stratum spinosum | Lower stratum spinosum | Stratum basale | Dermis |
|---|---|---|---|---|---|
| Normal (14) | 2.3 | 0.5 | 0 | 0 | 0 |
| Psoriasis (12) | 0.1 (12)[+] | 1.3 (1) | 0.8 | 0 | 0.1 |
| Atopic dermatitis (21) | 0.4 (21) | 1.1 (5) | 0.6 | 0 | 0.1 |
| Ichthyosis vulgaris (6) | 1.8 (5) | 0.7 (1) | 0 | 0 | 0 |
| Cellulitis (3) | 1.4 (3) | 1.8 (0) | 0.6 | 0 | 1.1 |
| DLE (4) | 1 (4) | 0.9 (0) | 0.1 | 0 | 0.2 |
| Acne (1) | 1.8 (1) | 1.9 (0) | 0.4 | 0 | 0 |

Fig.5

COMPOSITION FOR IMPROVING INFLAMMATORY DISEASE USING ABH ANTIGENS

CROSS-REFERENCE TO RELATED APPLICATIONS

This application is a U.S. national stage entry under 35 U.S.C. §371 of PCT International Patent Application No. PCT/KR2010/000103, filed Jan. 7, 2010, and claims priority to Korean Patent Application No. 10-2009-0002078, filed Jan. 9, 2009, the contents of which are incorporated herein by reference in their entirety.

TECHNICAL FIELD

The present invention relates to a composition for improving inflammatory disease, more specifically to a composition for improving inflammatory disease to improve inflammatory reactions and the barrier function of skin, to enhance aging resistance and skin elasticity, and to prevent or treat aging.

BACKGROUND ART

ABH antigen is the antigen that determines ABO blood type. ABO blood type is determined by the difference of ABO gene activity in glycosylated terminal having a specific structure. ABH antigen is mainly expressed on the surface of erythrocyte, so it is a major reason that causes rejection when different type of blood is transfused. It is also known that ABH antigen is expressed in diverse tissues including blood vessel, salivary gland, sweat gland, small intestine, large intestine, and pancreas, in addition to erythrocyte. In normal skin tissues, this antigen is found mostly in granular layer where differentiation of keratinocytes is most progressed and in the cells right before granular layer, while ABH antigen is hardly observed in spinous layer and basal layer (Ravn et al., *APMIS* 108:1-28 (2000); Lloyd, *Glycoconjugate J* 17:531-541 (2000); Greenwell, *Glycoconjugate J* 14:159-173 (1997); Dabelsteen et al., *J Invest dermatol* 82:13-17 (1984)).

ABH antigen is determined according to the structure of glycosylated terminal of protein or lipid. When N-acetylgalactosamine is conjugated on fucose-galactose terminal, the antigen is determined as antigen A (type A). When galactose is conjugated, the antigen is determined as antigen B (type B). When N-acetylgalactosamine and galactose are all conjugated, the antigen is determined as type AB. When N-acetylgalactosamine and galactose are not conjugated, the antigen is determined as antigen O (type O) (see FIG. 1). Therefore, histological expression is regulated by the expression of fucosyl transferase 1 or 2 (FUT1 or FUT2) that regulates the synthesis of the common fucose-galactose terminal.

Efforts have been made to explain the rejection response according to the blood transfusion with different blood type, and to disclose corelationship between the expression of ABH antigen and incidence of diverse diseases. However, none of these efforts have been successful so far, and the function of ABH antigen itself still needs to be studied.

DISCLOSURE

Technical Problem

It is an object of the present invention to provide a composition for improving inflammatory disease comprising ABH antigen or a substance that can regulate the expression of ABH antigen as an active ingredient.

Technical Solution

To achieve the above object, the present invention provides a composition for improving inflammatory disease comprising ABH antigen or a substance that can regulate the expression of ABH antigen as an active ingredient. In this invention, the inflammatory disease includes such disease as inflammatory skin disease and inflammation in stomach, esophagus, small intestine, urethra, and conjunctiva, but not always limited thereto. The composition of the present invention is preferably in the form of pharmaceutical composition or cosmetic composition, but not always limited thereto.

In this description, the term "ABH antigen" indicates not only ABH antigen itself but also ABH antigen analogue and ABH antigen/ABH antigen analogue conjugate. The term "ABH antigen analogue" can be a substance that has the glycosylated structure having the reactivity to ABH antigen or the one having the similar structure so as to copy or suppress the physiological function of ABH antigen or the substance that includes an additional conjugate of such analogue fixed on a specific carrier molecule. For example, ABH antigen analogue is the substance in which one or more compounds such as monosaccharides or amino acids are additionally conjugated on ABH antigen, which is functioning like the original ABH antigen. ABH antigen is exemplified by such monosaccharides as fucose, galactose, glucose, N-acetylgalactosamine, and N-acetylglucosamine; and a mixture which is the combination of the monosaccharides (for instance, FG (Fucose:Galactose=1:1, H-antigen), FGG (Fucose:Galactose=1:2, B-antigen) or FGGN (Fucose:Galactose:N-acetylgalactosamine=1:1:1, A-antigen)), but not always limited thereto. In FG, FGG, or FGGN, the ratio of each monosaccharide composing a mixture can be different from the above-mentioned ratio.

In this description, "the substance that regulates the expression of ABH antigen" indicates every substance that can up-regulate or down-regulate the expression of ABH antigen. The substance that can up-regulate the expression of ABH antigen includes any kinds of substances that can increase ABH antigen biosynthesis by increasing the expression or the activity of glycosylase of each stage of ABH antigen synthesis, for example ABO, FUT1, and FUT2, or any substance that increases ABH antigen biosynthesis by promoting the expression of ABH antigen conjugated protein, lipid, and saccharide. The substance that increases ABH antigen biosynthesis is exemplified by the gene encoding glycosylase of each stage of ABH antigen synthesis including ABO, FUT1, and FUT2, or the vector harboring the gene. Once the gene or vector is applied on skin, the expression of ABH antigen is up-regulated, leading to normalization of skin differentiation, suggesting that immune response is reinforced and immune system becomes balanced and the barrier function of skin is also reinforced, resulting in more healthy skin. The vector can be constructed by one of those methods well-known to those in the art, or simply purchased on the market. According to a preferred embodiment of the present invention, the substance that increases the expression of ABH antigen can be willow tree extract or Scutellaria radix extract (see FIG. 6 B).

In the meantime, the substance that can down-regulate the expression of ABH antigen includes any kinds of substances that can reduce the expression or the activity of glycosylase of each stage of ABH antigen biosynthesis including ABO, FUT1, and FUT2, or any substance that reduces ABH antigen biosynthesis by suppressing the expression of ABH antigen conjugated protein, lipid, and saccharide. The substance that can reduce ABH antigen biosynthesis is exemplified by siRNA, shRNA, or the vector containing siRNA, shRNA, or antisense coding sequence that can suppress the expression of glycosylase of each stage of ABH antigen synthesis. Once the gene or the vector is applied on skin, the expression of ABH antigen is down-regulated, and as a result Th1 inflammation reaction is suppressed, suggesting that excessive inflammation reaction is alleviated to relieve symptoms of inflammatory disease. The vector can be constructed by one of those methods well-known to those in the art, or simply purchased on the market. According to a preferred embodiment of the present invention, the substance that can reduce the expression of ABH antigen can be *Acanthopanax senticosus* extract, *Cirsium japonicum* extract, *Lentinus edodes* extract, ginseng extract, or *Echinacea purpurea* extract (see FIG. 6A).

The composition of the present invention preferably includes ABH antigen or the substance that can regulate the expression of ABH antigen at the concentration of 0.001-10 weight % by the total weight of the composition. If the content of the substance is less than 0.001 weight %, inflammatory disease improving effect will be not good enough. On the other hand, if the content of the substance is more than 10 weight %, miscibility with other ingredients and formulation stability might be in question. Therefore, the preferable content of ABH antigen or the substance that can regulate the expression of ABH antigen is 0.01-5 weight %.

The inflammatory disease on which the present invention can be applied is exemplified by inflammatory skin disease, and inflammation in other tissues such as stomach, esophagus, small intestine, urethra and conjunctiva, but not always limited thereto. The skin disease herein includes psoriasis, atpoic dermatitis, ichthyosis, pemphigus, acne, lupus erythematosus, skin aging, wrinkles, etc, but not always limited thereto. In fact, any disease caused by inflammation on skin can be included in the criteria of this invention.

The dosage form of the composition of the present invention is not limited but is preferably an external preparation for skin. The preferable example of the external preparation for skin is skin, lotion, massage cream, nourishing cream, pack, gel or adhesive type cosmetic composition. A transdermal preparation such as lotion, ointment, gel, cream, patch or spray is also preferable formulation. The composition for external preparation in whatever forms can include any other ingredients in addition to the essential active ingredient, and these ingredients can be selected by those in the art considering the purpose or the formulation of the preparation.

When the composition of the present invention is applied in cosmetics, the composition contains skin scientifically acceptable medium or base. The proper formulation can be exemplified by solution, gel, solid or dough anhydride, emulsion prepared by dispersing oil phase on water phase, suspension, microemulsion, microcapsule, microgranule, ionic (liposome) or non-ionic vesicle, cream, skin, lotion powder, spray, and conceal stick. In addition, the cosmetics can be formulated as an aerosol composition containing foam or compressed propellant. In addition, it can be formulated as a supplement for local or systemic application generally used in the field of skin science by containing skin scientifically acceptable medium or base.

The composition of the present invention can additionally include a supplement generally used in the field of skin science such as fatty substance, organic solvent, resolvent, concentrate, gelling agent, softener, antioxidant, suspending agent, stabilizer, foaming agent, odorant, surfactant, water, ionic or non-ionic emulsifying agent, filler, sequestering agent, chelating agent, preserving agent, vitamin, blocker, moisturing agent, essential oil, dye, pigment, hydrophilic or hydrophobic activator, lipid vesicle or other components generally used in cosmetology. The amount of the above supplement can be determined as generally accepted in the field of cosmetology.

When the composition of the present invention is applied in medicine, the composition contains ABH antigen or a substance that can regulate the expression of ABH antigen as an active ingredient. The composition of the present invention can be administered orally or parenterally and be used in general forms of pharmaceutical formulation. That is, the composition for improving inflammatory disease of the present invention can be prepared for oral or parenteral administration by mixing with generally used diluents or excipients such as fillers, extenders, binders, wetting agents, disintegrating agents and surfactants. Solid formulations for oral administration are tablets, pills, powders, granules and capsules. These solid formulations are prepared by mixing ABH antigen or the substance that can regulate the expression of ABH antigen with one or more suitable excipients such as starch, calcium carbonate, sucrose or lactose, gelatin, etc. Except for the simple excipients, lubricants, for example magnesium stearate, talc, etc, can be used. Liquid formulations for oral administrations are suspensions, solutions, emulsions and syrups, and the above-mentioned formulations can contain various excipients such as wetting agents, sweeteners, aromatics and preservatives in addition to generally used simple diluents such as water and liquid paraffin. Formulations for parenteral administration are sterilized aqueous solutions, water-insoluble excipients, suspensions, emulsions, lyophilized preparations and suppositories. Water insoluble excipients and suspensions can contain, in addition to the active compound or compounds, propylene glycol, polyethylene glycol, vegetable oil like olive oil, injectable ester like ethylolate, etc. Suppositories can contain, in addition to the active compound or compounds, witepsol, macrogol, tween 61, cacao butter, laurin butter, glycerol, gelatin, etc, but not always limited thereto.

In this invention, the active ingredient can be formulated according to the conventional method, and at this time, generally used supplements such as surfactants, excipients, coloring agents, flavors, preserving agents, stabilizing agents, buffers, and suspending agents, can be properly used.

The dosage of ABH antigen or the substance that regulates the expression of ABH antigen, used as an active ingredient for the composition of the present invention, can be determined according to age, gender, and weight of a patient, target disease or pathology, severity of disease, administration pathway, and the opinion of a prescriber. The determination of dosage based on the factors can be made by those in the art. General formulations except injection can be locally applied by the decision of those in the art. And injection can be locally injected in the corium and subcutaneous fat, but not always limited thereto. In general, the dosage is determined in the range of 0.001 mg/kg/day-2,000 mg/kg/day. The more preferable dosage is 1 μg/kg/day-100 μg/kg/day. The dosage units can contain, for example, 1, 2, 3 or 4 individual doses or ½, ⅓ or ¼ of an individual dose. An individual dose preferably contains the amount of active compound which is administered in one application and which usually corresponds to a whole, ½, ⅓ or ¼ of a daily dose.

In a preferred embodiment of the present invention were investigated various inflammatory skin diseases including abnormal inflammation reaction on skin caused by diverse genetic/environmental causes and other inflammatory disorder accompanying immune system imbalance and abnormal keratinocyte differentiation which are exemplified by psoriasis, atpoic dermatitis, ichthyosis, and pemphigus. As a result, it was observed that ABH antigen was either hardly expressed in granular layer or abnormally expressed by abnormal differentiation of keratinocytes (see FIG. 4 and FIG. 5). This abnormal differentiation of keratinocytes into granular layer observed in diverse skin diseases might be a major reason causing problems in skin barrier function. When UV was irradiated on normal skin twice as strong as the minimum inflammation inducing strength, the expression of ABH antigen in granular layer was no more observed on day three (see FIG. 3).

In another preferred embodiment of the present invention, a variety of natural substance extracts were treated to keratinocytes. *Acanthopanax senticosus, Cirsium japonicum, Lentinus edodes, ginseng*, and *Echinacea purpurea* extracts reduced the expression of blood type related antigen, while willow tree extract and *Scutellaria radix* extract rather increased the expression of blood type related antigen (see FIG. 6). The substance that increased the expression of blood type related antigen can be used to increase immunity, and in the meantime, the substance that reduced the expression of blood type related antigen can be used to suppress excessive inflammatory reaction. It was also investigated what effect the administration of ABH antigen or ABH antigen-constituting monosaccharides could bring on the expression of blood type related antigen. As a result, when ABH antigen or ABH antigen-constituting monosaccharide was treated, the expression of blood type related sugars was increased in cells and skin (see FIGS. 7-9). From the above results, it was confirmed that the expression of ABH antigen is co-related closely with the differentiation of keratinocytes and inflammation on skin.

In another preferred embodiment of the present invention, the expression of ABH antigen was artificially eliminated. At that time, it was observed that Th1 immune response mediated by interferon-γ was suppressed (see FIGS. 10-12). In another experiment, TNF-α and IL-1β were treated after the expression of ABH antigen was suppressed. In that case, the expression of BD-2 gene that was high in the control was reduced (see FIG. 13). In another example, when the expression of ABH antigen was inhibited, moving speed of keratinocytes was slow down (see FIG. 14). Considering the progressive stages of atopic dermatitis, it was observed in the primary stage that Th1 inflammation reaction was reduced whose cause was not disclosed but presumed to be the imbalance of cytokine regulating inflammation reaction. Then, in the following stage, Th2 inflammation reaction was rapidly amplified which accompanied up-regulation of immunoglobulin E (IgE) whose antigen has not been clearly identified, yet. At that time, decrease of the expression of ABH antigen in granular layer that might be caused by different reasons seemed to be a part of the reasons for the decrease of primary Th1 inflammation reaction. So, it was suggested that skin disease such as atopic dermatitis could be prevent or treated by correcting the expression of abnormal ABH antigen. When normal skin is continuously exposed on inflammation reaction caused by various dermal irritations, skin tissues are exposed continuously on active oxygen, and accordingly, skin tissues are damaged, wrinkled, and aged rapidly. Therefore, skin damage, wrinkles, and skin aging can be prevented by reducing active oxygen by soothing and controlling skin inflammation reaction properly.

In a variety of inflammatory skin diseases, when ABH antigen is deficient, abnormal inflammation reaction occurs. As a result, normal skin differentiation and original defensive system of skin can be damaged. So, if ABH antigen is provided intentionally from outside or a substance that can increase the expression of ABH antigen is added, normal immune response will be strengthened. That is, if the expression of ABH antigen is increased in granular layer, immune response in skin will be strengthened, so that either temporary or genetic ABH antigen expression diminution will be supplemented to maintain skin immune system normally, leading to the prevention and treatment of various skin diseases caused by unbalanced abnormal skin immune system, and thus it will help to maintain skin healthy by strengthening skin barrier function.

The present invention provides a screening method for a dermatologically useful substance including the step of selecting a substance from many candidates that can either increase or decrease the expression of ABH antigen by accelerating the differentiation of epidermal keratinocytes in vivo or in vitro. Particularly, all the candidates were treated to cells equally under the same condition, followed by cell culture. ABH antigen was quantified by Western blotting, leading to the selection of qualified candidates. Besides, any conventional screening method used for the selection of valuable proteins that is well informed to those in the art can be used herein.

The present invention also provides a skin care method including the ways of enhancing endogenous immune response by up-regulating ABH antigen in granular layer of skin and by promoting antimicrobial peptide expression and enhancing skin barrier function.

The present invention also provides a method for soothing skin inflammation including the step of alleviating symptoms of skin disease caused by excessive inflammatory response by suppressing the expression of Th1 inflammatory response related factors by reducing the expression of ABH antigen temporarily.

The present invention also provides a method for recovering immune functions on skin including the step of suppressing imperfect differentiation of keratinocytes and abnormal inflammatory response by controlling immune response to be normal by increasing the expression of normal ABH antigen in granular layer of the skin with weakened immunity.

Advantageous Effect

The composition of the present invention has the effect of improving or relieving symptoms of inflammatory disease carrying inflammation in diverse tissues including skin. Therefore, it can be helpful for maintaining skin healthy by accelerating antimicrobial peptide expression and by enhancing skin barrier function and at the same time for the recovery of damaged skin from skin disease. Furthermore, the composition of the invention can prevent or improve aging by suppressing inflammatory reaction continuously and at the same time strengthen skin elasticity and prevent or improve wrinkles on skin. Thus, the composition of the invention can be effectively used for the screening of a useful substance that can improve inflammatory skin disease and aging.

DESCRIPTION OF DRAWINGS

The application of the preferred embodiments of the present invention is best understood with reference to the accompanying drawings, wherein:

FIG. 1 is a schematic diagram illustrating the chemical structure of blood type sugar.

FIG. 5 is a table illustrating the result of immunohistochemical staining with skin tissues having diverse skin diseases.

MODE FOR INVENTION

Practical and presently preferred embodiments of the present invention are illustrative as shown in the following Examples.

However, it will be appreciated that those skilled in the art, on consideration of this disclosure, may make modifications and improvements within the spirit and scope of the present invention.

Experimental Example 1

Investigation of the Expression of ABH Antigen in Different Human Tissues

Biopsy was performed to obtain different human tissues from various parts of human body. Immunohistochemical staining was performed by using ABH antigen specific antibody in order to investigate the expression of ABH antigen in each tissue. Particularly, the tissues obtained from biopsy were fixed in 10% formalin for overnight. Then, formalin was removed and the tissues were dehydrated, so as to make paraffin block. The tissue block was sliced into 0.4 μm thick sections, which were placed on slide. The slide was loaded in a 58° C. dry oven for one hour to melt paraffin. To eliminate paraffin completely, the slide was treated with xylem 4 times, 5 mines for each time, and then the slide was soaked in 100% ethanol twice, 1 minute for each, in 95% ethanol for 1 minute, in 80% ethanol for 1 minute, and in 70% ethanol for 1 minute, leading to stepwise rehydration. The slide was washed with running tap water for 5 minutes and then washed again with distilled water for 5 more minutes. It was transferred into pH 6.0 TRS (Dao), and autoclaved at 120° C. for 10 minutes. The tissues were cooled down by double boiling for 10 minutes, followed by washing with distilled water for 5 minutes twice. Then, the tissues were washed again with PBS for 5 minutes and then transferred into 3% oxygen peroxide solution diluted with PBS for 10 minutes. The tissues were washed with PBS three times, for 10 minutes each. PAP pen was used to draw a border of the tissue, and then the tissue was treated with blocking solution (Seemed) for 30 minutes. The primary antibody recognizing type A or type B antigen was treated to the tissue, which stood at 4° C. for 16 hours. The tissue was washed with PBS for 10 minutes, three times, and then treated with HRP (horseradish peroxides) conjugated secondary antibody (Santa Cruz) for 15 minutes. The tissue was washed again with PBS for 10 minutes, twice, and then washed with distilled water for 10 minutes, twice. Coloring was induced by using AEC coloring agent (Seemed), followed by washing again with running tap water for 5 minutes and then with distilled water for 5 minutes. Nuclei were stained with hematoxylin (Dako), followed by washing with running water for 10 minutes. Moisture around the tissue was eliminated, followed by mounting with aqueous mounting solution (Dako). Then, the tissue was observed under microscope and the photographs of the tissue were obtained.

Figure 2:
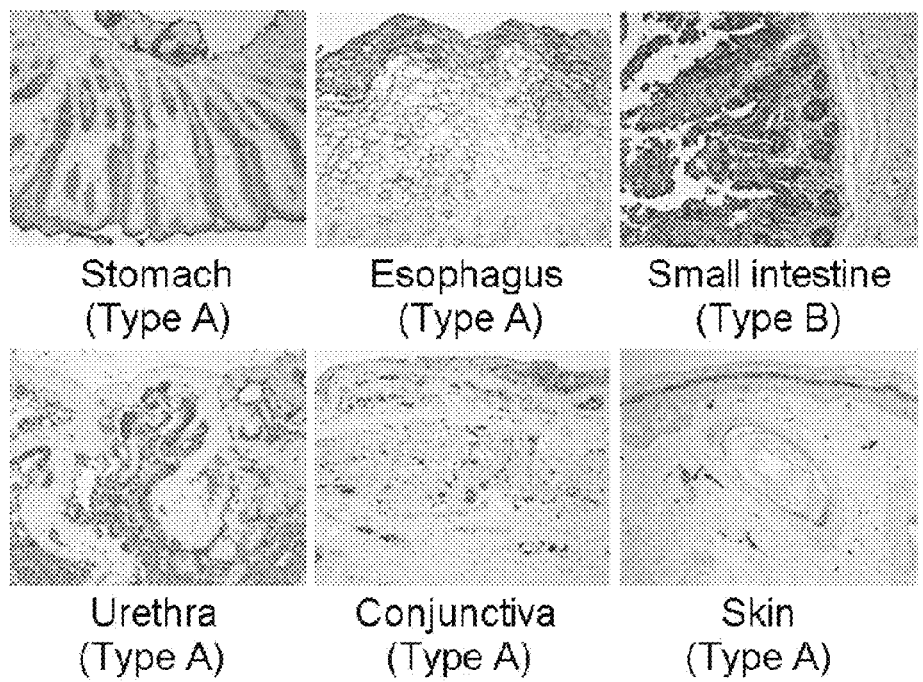
FIG. 2 is a set of photographs illustrating the expression of ABH antigen in normal tissues.

As a result, it was confirmed that ABH antigen was expressed not only in erythrocytes but also in many different tissues including stomach (type A), esophagus (type A), small intestine (type B), urethra (type A), conjunctiva (type A), and skin (type A) according to blood types (FIG. 2). The tissues of a person with blood type A were only stained by type A antigen specific antibody and not stained by type B antigen specific antibody. Likewise, the tissues of a person with blood type B were only stained by type B specific antibody. In the case of a person with blood type AB, the tissues were stained by both antibodies, while the tissues of a person with blood type O were not stained by either of them.

Experimental Example 2

Down-Regulation of the Expression of ABH Antigen by UV Irradiation

In normal tissues, the tissues of a person with blood type A are stained only by A antigen specific antibody, which usually takes place in granular layer in epidermis (Dabelsteen et al., *J Invest dermatol* 82:13-17 (1984)). Minimal erythema dose (MED), indicating the strength with which the first erythema is observed after UV irradiation, was measured individually. Each skin was irradiated by 2MED, and then skin biopsy was performed 0, 28, 48, and 72 hours after the UV irradiation. Immunohistochemical staining was performed by the same manner as described in Experimental Example 1 to investigate the expression of ABH antigen.

Figure 3:
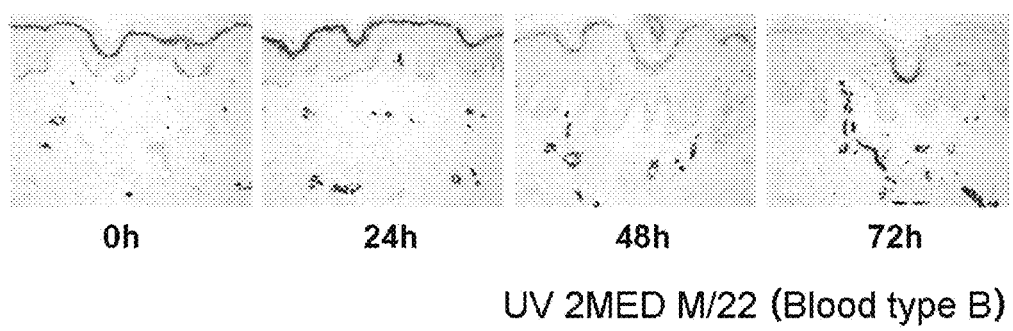
FIG. 3 is a set of photographs illustrating the down-regulation of ABH antigen (type B antigen) in irradiated skin.

As a result, ABH antigen was normally expressed until 24 hours after the UV irradiation. However, after 48-72 hours, the expression of ABH antigen was gradually decreased (FIG. 3).

Experimental Example 3

Down-Regulation of the Expression of ABH Antigen in Various Skin Diseases

Based on the fact that the expression of ABH antigen is decreased by UV irradiation at the strength of inducing inflammation, the expression of ABH antigen was investigated in diverse skin diseases presumably carrying symptoms caused by irregulation of inflammation reaction. For the investigation, tissues were obtained by biopsy from patients having psoriasis (type A), atpoic dermatitis (type A), ichthyosis (type A), cellulitis (type A), discoid lupus (type A), acne (type B), etc. Immunohistochemical staining was performed with the tissues by the same manner as described in Experimental Example 1 to investigate the expression of ABH antigen.

Figure 4:
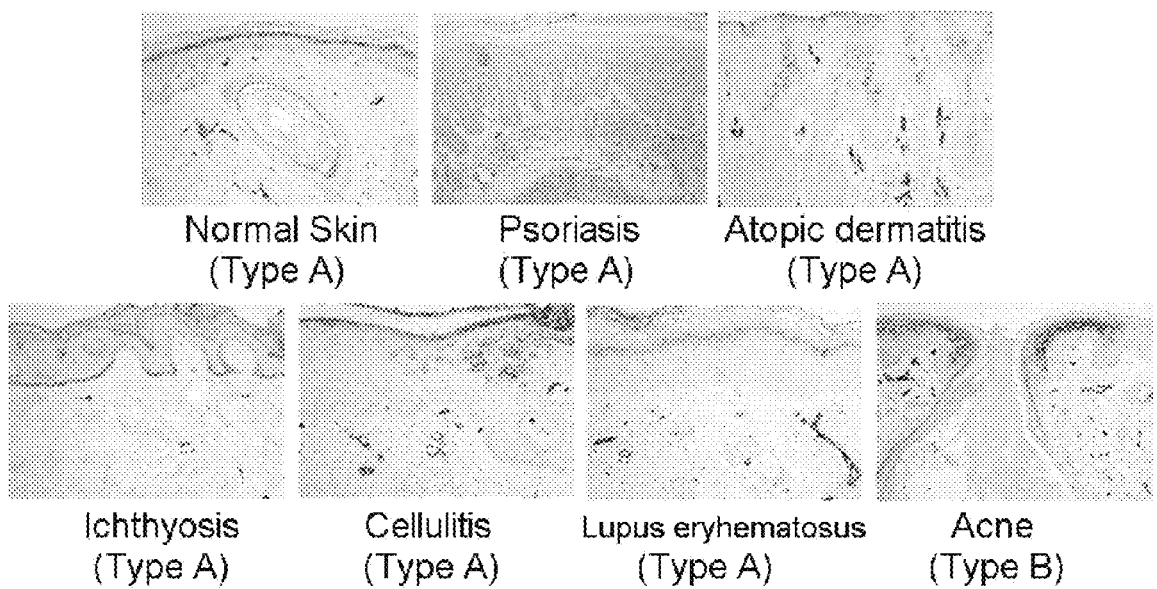
FIG. 4 is a set of photographs illustrating the expression of ABH antigen in skin tissues having diverse skin diseases.

As a result, the expression of ABH antigen in granular layer was deficient in most pathological tissues. In spite of individual difference, the expression of abnormal ABH antigen was commonly in spinous layer or basal layer (FIG. 4 and FIG. 5). This result indicates that there is incomplete differentiation in granular layer and/or abnormal differentiation in spinous layer or basal layer.

Experimental Example 4

Effect of Natural Extracts on the Expression of ABH Antigen

Effect of various natural extracts on the expression of ABH antigen was investigated. For the investigation, HaCaT cells were treated with undiluted extracts of *Acanthopanax senticosus, Cirsium japonicum, Lentinus edodes*, ginseng, *Echinacea purpurea, Scutellaria radix* and willow tree (purchased from Biospectrum) at the concentrations of 0.1% (v/v), 1% (v/v), and 2% (v/v) respectively, followed by culture for 48 hours. Then, Western blotting was performed to investigate type B antigen expression. As the control, alpha-tubulin or STAT1 alpha protein was used.

Figure 6:
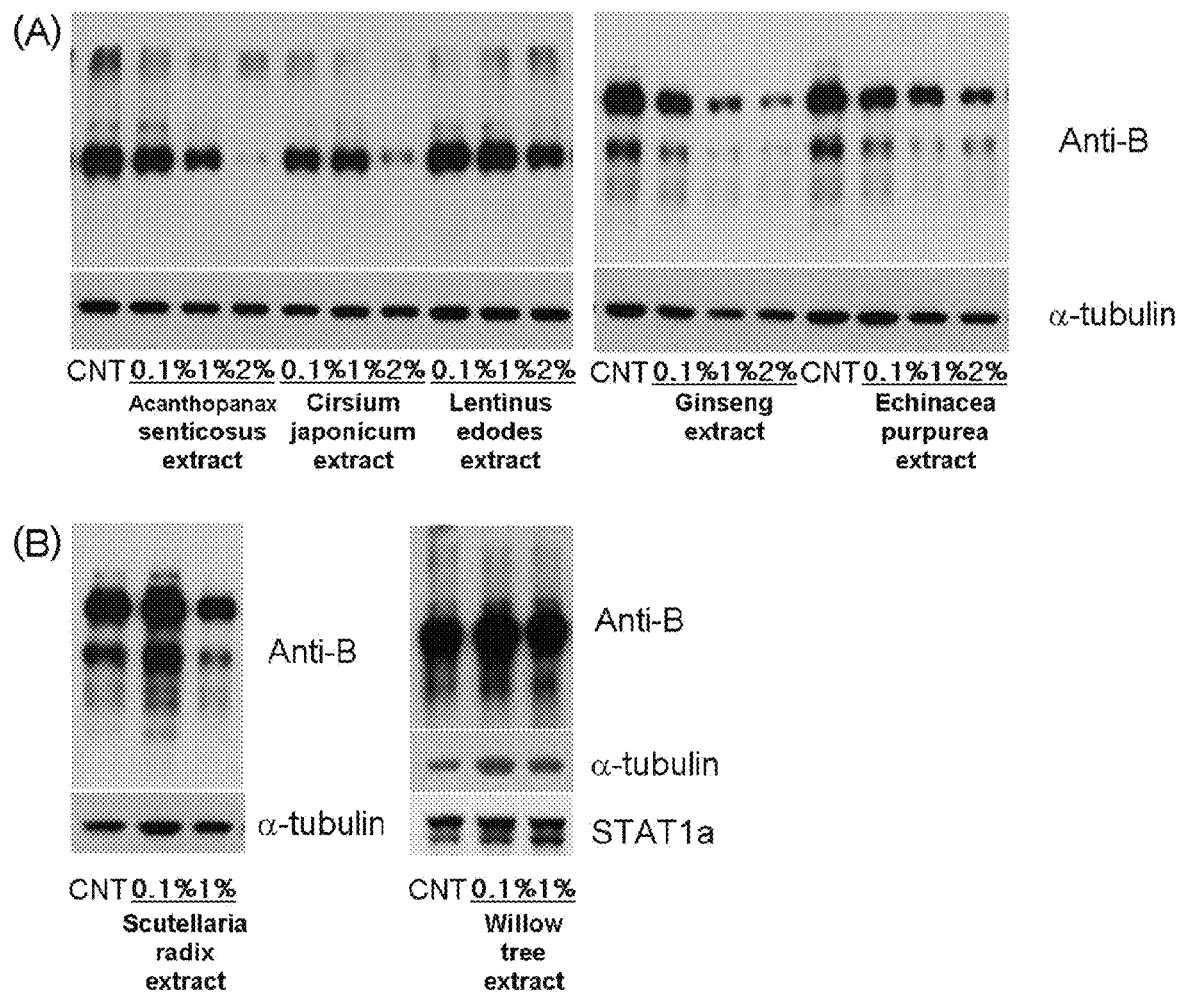
FIG. 6 is a set of electrophoresis photographs illustrating the effect of different natural extracts on the expression of ABH antigen.

As a result, the extracts of *Acanthopanax senticosus, Cirsium japonicum, Lentinus edodes*, ginseng and *Echinacea purpurea* reduced type B antigen expression in HaCaT cells, while the extracts of willow tree and *Scutellaria radix* extract increased type B antigen expression (FIG. 6).

Experimental Example 5

Effect of ABH Antigen on the Expression of Blood Type Antigen

Figure 7:
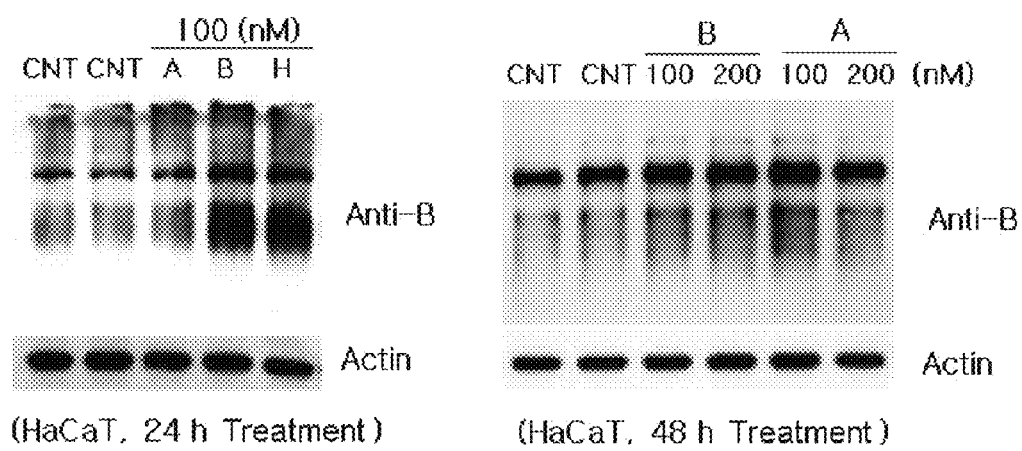
FIG. 7 is a set of electrophoresis photographs illustrating the effect of ABH antigen treatment on the expression of blood type antigen.
Figure 8:
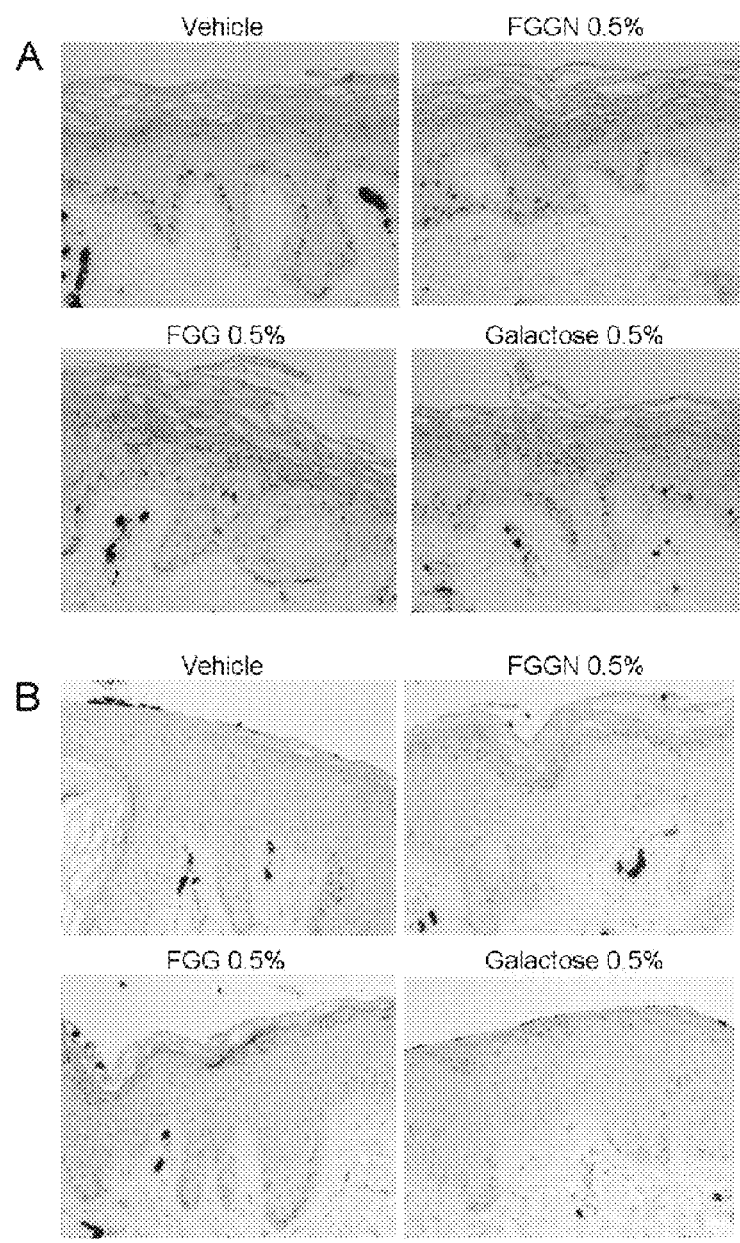
FIG. 8 is a set of photographs of immunohistochemical staining illustrating the effect of the administration of ABH antigen-constituting monosaccharides on the expression of blood type antigen.

A, B, and H antigens (purchased from Dextra Laboratories) were treated to HaCaT cells harboring B antigen at the concentration of 100 nM for 24 hours, followed by Western blotting to investigate the expression of B antigen. As a result, the expression of B antigen was increased by B or H antigen. A antigen did not increase the expression of type B antigen (FIGS. 7-10). When A or B antigen was treated to HaCaT cells at the concentration of 100 nM or 200 nM for 48 hours, the expression of type B antigen was increased by A or B antigen (FIG. 7). The above results indicate that A, B, and H antigens could increase the expression of type B antigen in HaCaT cells.

Experimental Example 6

Effect of Administration of ABH Antigen-Constituting Monosaccharides on the Expression of Blood Type Antigen (1)

It is a general phenomenon that the expression of blood type antigen is reduced in buttock skin of an atopic dermatitis patient, compared with in normal people, even if a clear lesion is not observed by the naked eye there. It was investigated whether the reduced expression was recovered by the administration of monosaccharides which constitute ABH antigen. To do so, the sugar mixture composed of 100% galactose, FGG (Fucose:Galactose=1:2, B-antigen composition) and FGGN (Fucose:Galactose:N-acetylgalactosamine=1:1:1, A-antigen composition) was dissolved in the mixed solvent composed of polyethyleneglycol:ethanol:water=3.5:1.5:5 at the concentration of 0.5% (w/v). The lysate was closed-applied on buttock skin of type B male atpoic dermatitis patient at the age of 30 (volunteer) and type A male atpoic dermatitis patient at the age of 24 (volunteer) for 48 hours, which was repeated again (total 96 hours). Then, biopsy was performed to obtain sample tissues. Immunohistochemical staining was performed with the tissues by the same manner as described in Experimental Example 1 to investigate the expression of ABH antigen.

As a result, when substances forming blood type sugar were treated, the expression of blood type sugar was increased both in cells and skins of type B male atpoic dermatitis patient at the age of 30 (volunteer) (FIG. 8A) and type A male atpoic dermatitis patient at the age of 24 (volunteer) (FIG. 8B).

Experimental Example 7

Effect of Administration of ABH Antigen-Constituting Monosaccharides on the Expression of Blood Type Antigen (2)

Figure 9:
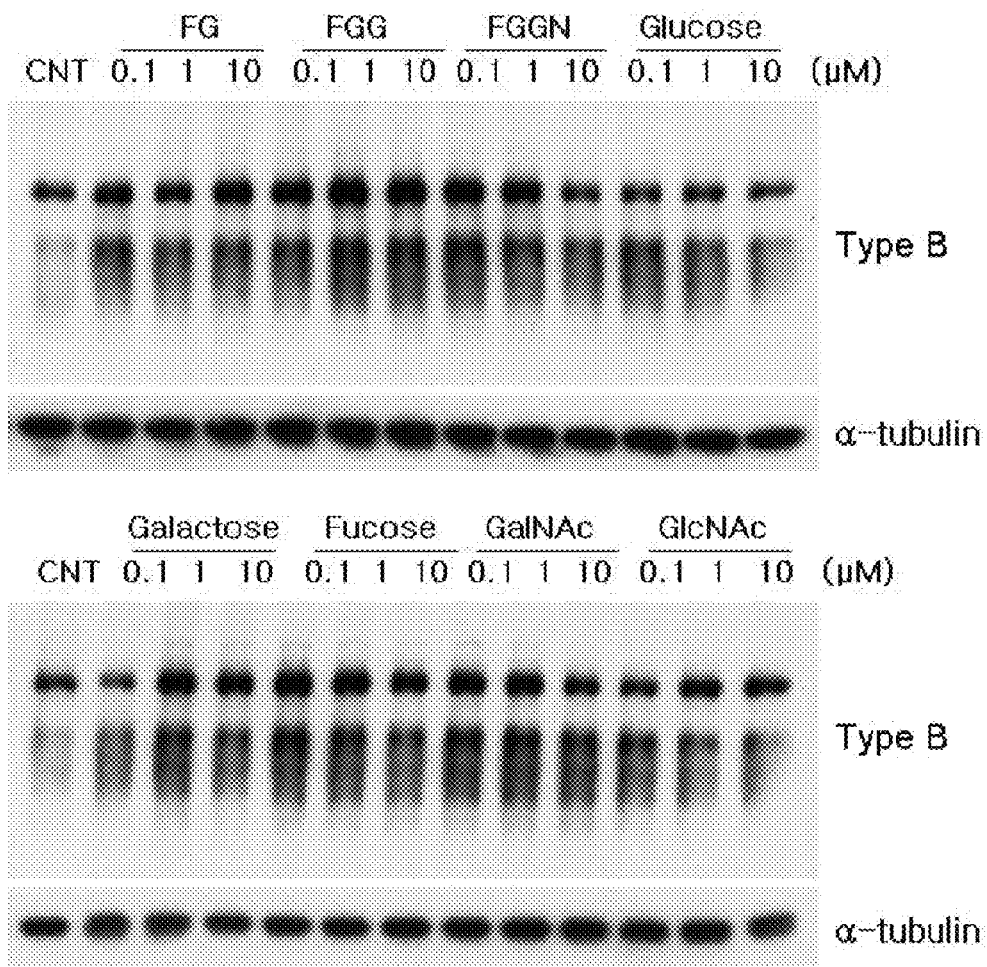
FIG. 9 is a set of electrophoresis photographs illustrating the effect of the administration of ABH antigen-constituting monosaccharides on the expression of blood type antigen.

HaCaT cells harboring B antigen was treated respectively with FGG and FGGN mixture and FG (Fucose:Galactose=1:1, H-antigen composition) mixture which compose A, B, and H antigen, and also glucose, galactose, fucose, N-acetylgalactosamine and N-acetylglucosamine which are monosaccharides that constitute A, B, and H antigen at different concentrations of 0.1, 1, and 10 μM for 24 hours. Western blotting was performed to investigate the expression of B antigen. As a result, the expression of B antigen was increased in every case above (FIG. 9).

Experimental Example 8

Decrease of ICAM-1 and HLA-DR Expression by Elimination of ABH Antigen

In general, interferon-γ(IFNg), Th1 cytokine, playing an important role in inflammation reaction in skin increases the expressions of various factors mediating Th1 immune response. In particular, when keratinocytes play a role as antigen presenting cells, ICAM-1 and HLA-DR are the most important molecules (Barker et al., *Lancet* 337:211-214 (1991)). HaCaT, the keratinocyte cell line harboring B antigen was cultured in DMEM (Dulbecco's modification of Eagle's medium, Welgene) supplemented with 5% FBS (Fetal bovine serum, Hyclone) in an incubator until the cells were grown to fill 70% of 35 mm culture dish. Then the cells were incubated in Opti-MEM (Invitrogen) for 2 hours, followed by transfection with 250 p mol of the negative control RNA (Bioneer) that had no target gene and with the same amount of siRNA (Bioneer, SEQ. ID. NO: 1) targeting FUT1 gene by using 2.5 μl of lipofectamine 2000 (Invitrogen). The medium was replaced next day with FBS free DMEM. On the next day, the cells were treated with interferon-γ (Peprotech) at the concentration of 10 ng/ml. Protein was extracted from the cells at the time points of 0, 12, 15, 18, 24, 36, and 48 hour. Western blotting was performed by using each corresponding antibody (Abcam, Dako) to investigate the expression of type B antigen (down-regulation) and the changes of ICAM-1 and HLA-DR, the major factors of antigen presenting cells. Alpha-tubulin (SantaCruz) was used as the control protein that was hardly changed.

Figure 10:
FIG. 10 is a set of Western blot photographs illustrating the down-regulations of ICAM-1 and HLA-DR by the elimination of ABH antigen.

As a result, the expressions of ICAM-1 and HLA-DR were remarkably increased by interferon-γ in the control, while the expression of ICAM-1 was significantly suppressed by interferon-γ in the experimental group which was treated with 250 p mol/ml of FUT1 siRNA to suppress the expression of type B antigen. In addition, the up-regulation of HLA-DR was inhibited up to 18th hour, and the up-regulation was recovered after 24 hours to the time point of 48 hour (FIG. 10).

Experimental Example 9

Decrease of IL-8, GM-CSF and BD-2 Expression by Elimination of ABH Antigen

HaCaT, the keratinocyte cell line harboring B antigen, was treated with lipofectamine 2000 (control, CNT), and transfected with 250 p mol of negative control RNA (NC), SiRNA (Bioneer) targeting FUT1 (SiFUT1), and SiRNA (Bioneer) targeting ABO (SiABO) by the same manner as described in Example 4, resulting in 4 kinds of samples, which were treated or not treated with interferon-y at the concentration of 10 ng/ml. 24 hours later, RNA was extracted from the cells. The mRNA levels of IL-8, GM-CSF, and BD-2 (β-defensin 2) modified with 36b4 were confirmed by RT-PCR (Applied Biosystems, 7500 Real-Time PCR system) using sybrgreen (Takara master mix). At this time, the siRNA sequence of FUT1 gene was the same as the one of Experimental Example 4 and the siRNA sequence of ABO gene was the nucleotide sequence represented by SEQ. ID. NO: 2. The primers for human IL-8 were the nucleotide sequences represented by SEQ. ID. NO: 3 and NO: 4. The primers for GM-CSF were the nucleotide sequences represented by SEQ. ID. NO: 5 and NO: 6. The primers for BD-2 were the nucleotide sequences represented by SEQ. ID. NO: 7 and NO: 8.

Figure 11:
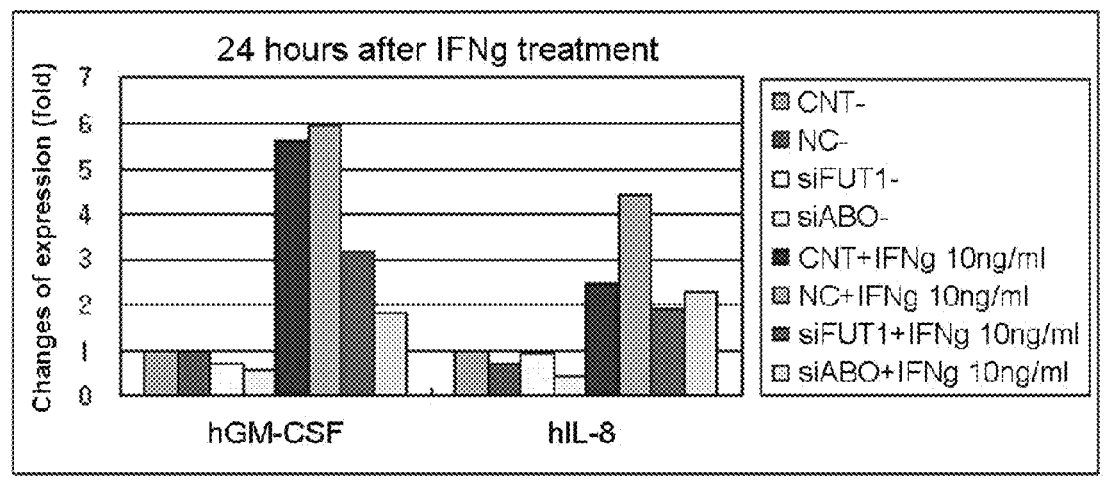
FIG. 11 is a graph illustrating the result of real-time PCR, in which the down-regulations of IL-8 and GM-CSF by the elimination of ABH antigen were confirmed.
Figure 12:
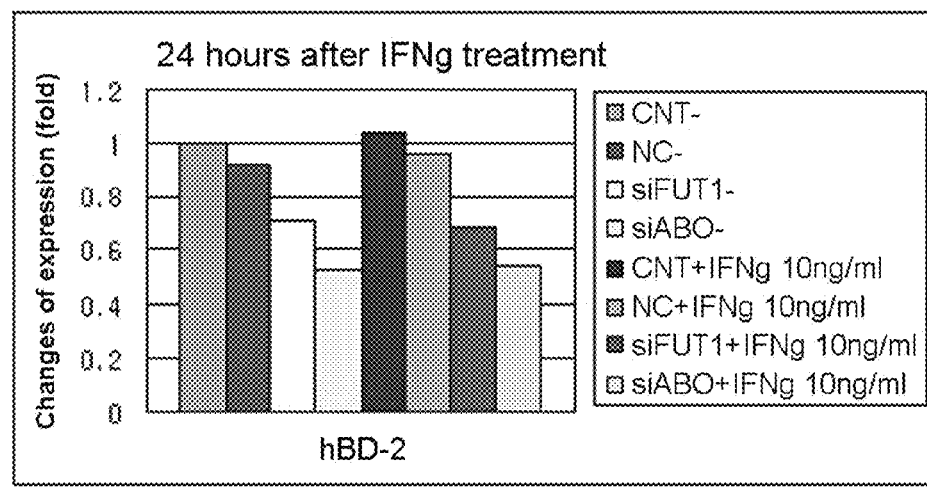
FIG. 12 is a graph illustrating the result of real-time PCR, in which down-regulation of BD-2 by the elimination of ABH antigen was confirmed.

As a result, among many factors mediating Th1 immune response, the expressions of IL-8 and GM-CSF induced by interferon-y were reduced by the elimination of type B antigen. The expression of BD-2, one of antimicrobial peptides of skin, was not increased by interferon-γ but decreased by the elimination of type B antigen (FIG. 11 and FIG. 12).

Experimental Example 10

Inhibition of BD-2 Expression by TNF-α or IL-1β Treatment after Elimination of ABH Antigen HaCaT cell line was transfected respectively with the lentivirus vector capable of over-expressing FUT1 siRNA and with the lentivirus vector (SantaCruz) capable of over-expressing ABO siRNA, followed by selective culture for one month with purmycin. As a result, HaCaT cell line suppressing FUT1 or ABO expression stably was constructed. The cells were treated with TNFα and IL-1β for 24 hours respectively. Then, the expression level of BD-2 mRNA was modified with 36b4 gene expression, followed by RT-PCR by the same manner as described in Experimental Example 7.

Figure 13:
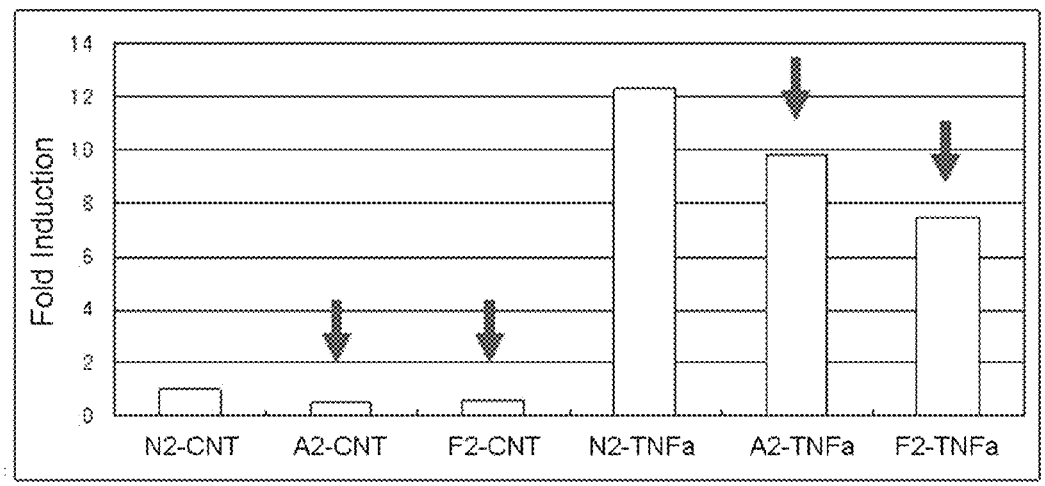
FIG. 13 is a set of graphs illustrating the suppression of BD-2 expression by the treatment of TNF-α or IL-1β after the elimination of ABH antigen.
Figure 13:
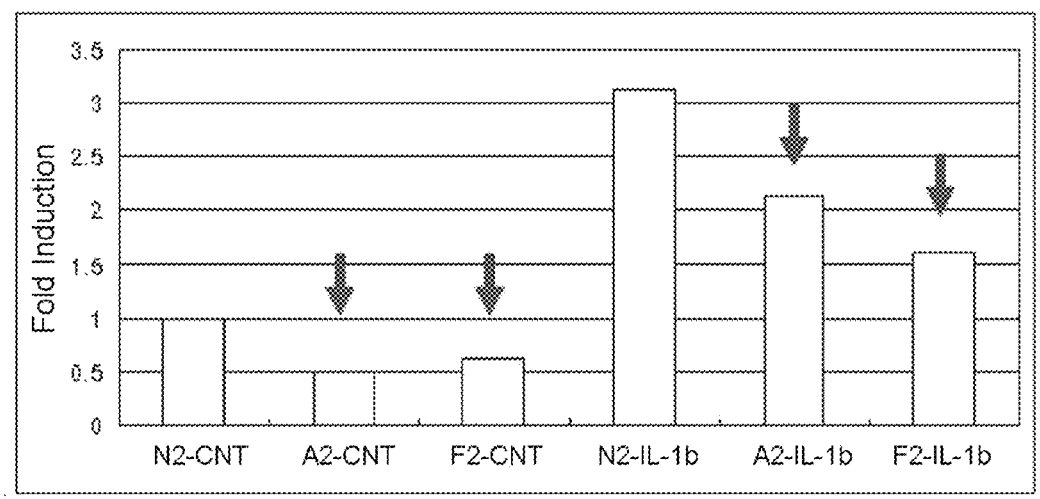

As a result, not only BD-2 expression non-treated with anything but also increased BD-2 expression mediated by inflammatory reaction after being treated with TNF-α and IL-1β were reduced to some degree in the HaCaT cell line suppressing FUT1 or ABO expression (FIG. 13).

Experimental Example 11

Effect of the Expression of ABH Antigen on Cell Migration Speed

HaCaT cell line was not treated with siRNA or transfected with the negative control siRNA (NC), FUT1 or ABO siRNA by the same manner as described in Experimental Example 4 by using lipofectamine 2000, followed by culture until the cells were grown to fill culture dish. Scratches were made at a regular interval to make room without cells. While the cells were cultured in DMEM supplemented with 10% FBS, pictures were taken at the time points of 0, 24, 48, 72, and 96 hour to observe cell migration.

Figure 14:
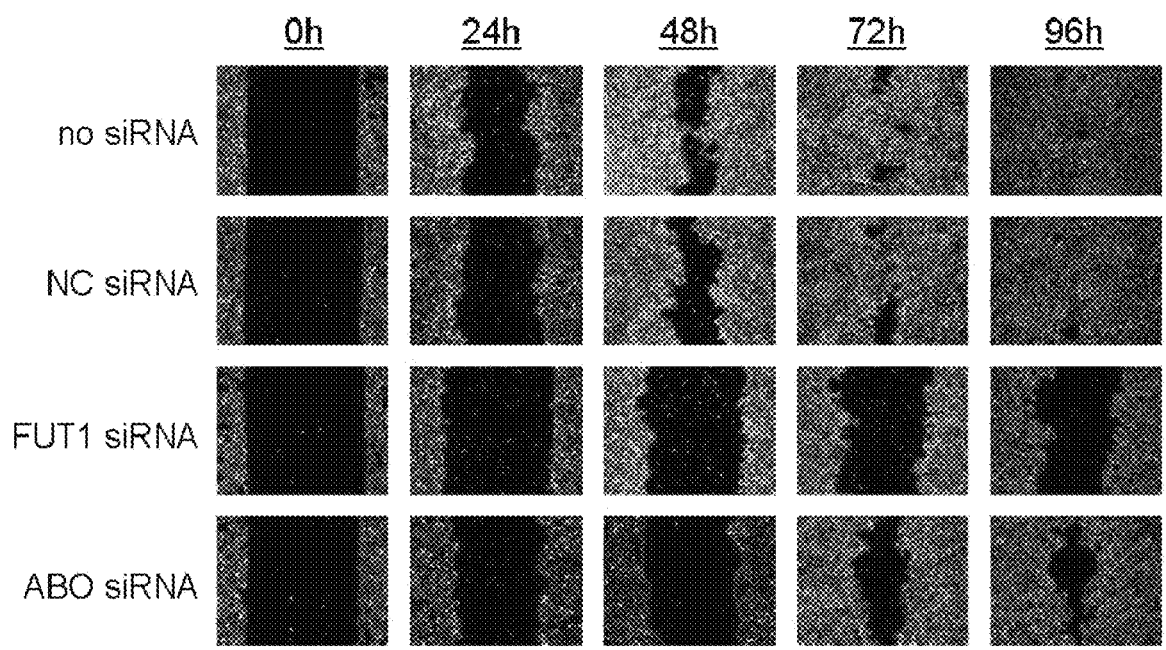
FIG. 14 is a set of photographs illustrating the effect of ABH antigen expression on the speed of cell migration.

As a result, in the cells transfected with ABO or FUT1 siRNA, the speed of closing the scratch (filling up the scratch with cells) was significantly decreased, compared with that in the cells not treated with siRNA or transfected with NC siRNA. In the cells treated with FUT1siRNA, the speed of closing the scratch was even slower than that in the cells treated with ABO siRNA (FIG. 14). The above results indicate that during wound healing, migration speed of keratinocytes can be slow down when FUT1 and ABO expressions are decreased, that is the expression of blood type antigen is reduced.

As explained hereinbefore, based on the fact that the expression of ABH antigen is reduced in various inflammatory skin diseases, the present inventors suppressed the expression of ABH antigen in keratinocytes forcefully. As a result, the inventors confirmed that immune system was weakened according to the decrease of various Th1 immune response factors induced by interferon-γ. Therefore, it was confirmed that inflammatory reaction could be regulated by regulating the expression of ABH antigen.

Manufacturing Example 1

Preparation of Pharmaceutical Composition

<1-1> Preparation of Syrup

Syrup containing the active ingredient by 20% (weight/volume) was prepared as follows. First, type H antigen, saccharin, and glucose were dissolved in 80 g of warm water. The mixture was cooled down, to which a mixture of glycerin, saccharin, flavors, ethanol, sorbic acid and distilled water was added. Water was added to the mixture, making the total volume of it 100 ml.

The constituents of the syrup are as follows.

| | |
|---|---|
| Type H antigen | 20 g |
| Saccharin | 0.8 g |
| Glucose | 25.4 g |
| Glycerin | 8.0 g |
| Flavor | 0.04 g |
| Ethanol | 4.0 g |
| Sorbic acid | 0.4 g |
| Distilled water | Proper amount |

<1-2> Preparation of Tablet 250 g of type B antigen, 175.9 g of lactose, 180 g of potato-starch and 32 g of colloidal silicic acid were all mixed together. 10% gelatin solution was added to the mixture, which was then pulverized and filtered with 14-mesh sieve. The pulverized mixture was dried, to which 160 g of potato-starch, 50 g of talc and 5 g of magnesium stearate were added to prepare tablet.

The constituents of the tablet are as follows.

| | |
|---|---|
| Type B antigen | 250 g |
| Lactose | 175.9 g |
| Potato-starch | 180 g |

-continued

| | |
|---|---|
| Colloidal silicic acid | 32 g |
| 10% gelatin solution | |
| Potato-starch | 160 g |
| Talc | 50 g |
| Magnesium stearate | 5 g |

<1-3> Preparation of Injectable Solution

Injectable solution containing 10 mg of the active ingredient was prepared as follows.

1 g of type A antigen, 0.6 g of sodium chloride and 0.1 g of ascorbic acid were dissolved in distilled water to make 100 and of solution. The solution was put in a bottle and heated at 20 for 30 minutes for sterilization.

The constituents of the injectable solution are as follows.

| | |
|---|---|
| Type A antigen | 1 g |
| Sodium chloride | 0.6 g |
| Ascorbic acid | 0.1 g |
| Distilled water | Proper amount |

Manufacturing Example 2

Preparation of Cosmetic Composition

<2-1> Preparation of Emulsified Cosmetics

Emulsified cosmetics were prepared according to the composition shown in Table 1. The method for the preparation is as follows.

1) heating the mixture comprising the raw materials 1-9 at 65-70;
2) adding the raw material 10 to the mixture of step 1);
3) dissolving the mixture comprising the raw materials 11-13 by heating at 65-70;
4) slowly adding the mixture of step 2) during performing step 3), followed by emulsification at 8,000 rpm for 2-3 minutes;
5) dissolving the raw material 14 in water and then adding the solution to the mixture of step 4), followed by emulsification for 2 minutes;

6) weighing the raw materials 15-17, which were added to the mixture of step 5), followed by emulsification for 30 seconds; and 7) degassing the mixture of step 6) finished with the emulsification process and then cooling thereof at 25-35 to give emulsified cosmetics.

TABLE 1

| Composition | Emulsified formulation 1 | Emulsified formulation 2 | Emulsified formulation 3 |
|---|---|---|---|
| 1 Stearic acid | 0.3 | 0.3 | 0.3 |
| 2 Stearyl alcohol | 0.2 | 0.2 | 0.2 |
| 3 Glyceryl monostearate | 1.2 | 1.2 | 1.2 |
| 4 Wax | 0.4 | 0.4 | 0.4 |
| 5 Polyoxyethylenesorbitan monolauric acid ester | 2.2 | 2.2 | 2.2 |
| 6 Paraoxybenzoic acid methyl | 0.1 | 0.1 | 0.1 |
| 7 Paraoxybenzoic acid propyl | 0.05 | 0.05 | 0.05 |
| 8 Cetyl ethyl hexanoate | 5 | 5 | 5 |
| 9 Triglyceride | 2 | 2 | 2 |
| 10 Cyclomethicone | 3 | 3 | 3 |
| 11 Distilled water | to 100 | to 100 | to 100 |
| 12 Concentrated Glycerin | 5 | 5 | 5 |
| 13 Triethanolamine | 0.15 | 0.15 | 0.15 |
| 14 Polyacrylic acid polymer | 0.12 | 0.12 | 0.12 |
| 15 Pigment | 0.0001 | 0.0001 | 0.0001 |
| 16 Flavor | 0.10 | 0.10 | 0.10 |
| 17 Type A antigen | 0.0001 | 1 | 10 |

<2-2> Preparation of Solubilized Cosmetics

Solubilized cosmetics were prepared according to the composition shown in Table 2. The method for the preparation is as follows.

1) adding the raw materials 2-6 to the raw material 1 (purified water), which were dissolved by using Agi-mixer;

2) adding the raw materials 8-11 to the raw material 7 (alcohol) and completely dissolved; and 3) slowly adding the mixture of step 2) to the mixture of step 1), followed by solubilization.

TABLE 2

| Composition | solubilized formulation 1 | solubilized formulation 2 | solubilized formulation 3 |
|---|---|---|---|
| 1 Purified water | to 100 | to 100 | to 100 |
| 2 Concentrated glycerin | 3 | 3 | 3 |
| 3 1,3-butyleneglycol | 2 | 2 | 2 |
| 4 EDTA-2Na | 0.01 | 0.01 | 0.01 |
| 5 Pigment | 0.0001 | 0.0002 | 0.0002 |
| 6 Type B antigen | 0.1 | 5 | 5 |
| 7 Alcohol (95%) | 8 | 8 | 8 |
| 8 Paraoxybenzoic acid methyl | 0.1 | 0.1 | 0.1 |
| 9 Polyoxyethylene hydrogenated ester | 0.3 | 0.3 | 0.3 |
| 10 Flavor | 0.15 | 0.15 | 0.15 |
| 11 Cyclomethicone | — | — | 0.2 |

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

The invention claimed is:

1. A method for treatment of inflammatory skin disease selected from the group consisting of psoriasis, atopic dermatitis, ichthyosis, pemphigus, acne, skin aging and wrinkles in a subject comprising administering to the subject an amount of a composition comprising ABH antigen or a substance that increases the expression of ABH antigen which is a gene selected from the group consisting of ABO, FUT1 and FUT2 or a vector containing the gene as an active ingredient effective to treat the inflammatory skin disease.

2. The method according to claim 1, wherein the substance that increases the expression of ABH antigen is administered.

3. The method according to claim 1, wherein ABH antigen or the substance that increases the expression of ABH antigen is included in the composition at the concentration of 0.001-10 weight % by the total weight of the composition.

4. The method according to claim 1, wherein the composition is prepared in the form of a pharmaceutical composition or a cosmetic composition.

5. The method according to claim 4, wherein the composition is formulated as an external preparation for skin.

6. The method according to claim 4, wherein the cosmetic composition is selected from the group consisting of skin, nourishing skin, massage cream, nourishing cream, pack, gel, adhesive type cosmetic preparations, lotion, ointment, gel, cream, patch and spray.

7. The method according to claim 4, wherein the pharmaceutical composition is in the form for oral or parenteral administration selected from the group consisting of solid, semi-solid, and liquid formulations.

8. The method according to claim 1, wherein the ABH antigen is selected from the group consisting of type A antigen wherein N-acetylgalactosamine is conjugated on fucose-galactose terminal, type B antigen wherein galactose is conjugated on fucose-galactose terminal, type AB antigen wherein both N-acetylgalactosamine and galactose are conjugated on fucose-galactose terminal and type H antigen wherein both N-acetylgalactosamine and galactose are not conjugated on fucose-galactose terminal.

9. The method according to claim 1, wherein the ABH antigen is selected from the group consisting of fucose, galactose, glucose, N-acetylgalactosamine, N-acetylglucosamine, FG (Fucose:Galactose =1:1, H-antigen composition), FGG (Fucose:Galactose =1:2, B-antigen composition) and FGGN (Fucose:Galactose:N-acetylgalactosamine =1:1:1, A-antigen composition).

* * * * *